United States Patent [19]
Wiegand

[11] 3,962,287
[45] *June 8, 1976

[54] CHEMICAL PROCESS FOR PRODUCING CITRIC ACID
[75] Inventor: Karl E. Wiegand, Baton Rouge, La.
[73] Assignee: Ethyl Corporation, Richmond, Va.
[ * ] Notice: The portion of the term of this patent subsequent to Oct. 30, 1990, has been disclaimed.
[22] Filed: Mar. 13, 1973
[21] Appl. No.: 340,725

Related U.S. Application Data
[63] Continuation-in-part of Ser. No. 172,627, Aug. 18, 1971, Pat. No. 3,769,337.

[52] U.S. Cl. ............................................. 260/535 P
[51] Int. Cl.² ........................................ C07C 59/16
[58] Field of Search ............................... 260/535 P

[56] References Cited
UNITED STATES PATENTS
3,769,337   /0000   Weigand ............................ 260/535

Primary Examiner—Paul J. Killos
Attorney, Agent, or Firm—Donald L. Johnson; John F. Sieberth; Shelton B. McAnelly

[57] ABSTRACT
It is disclosed that citric acid or its salts are obtained by the hydrolysis of an alkaline earth metal adduct obtained by reacting a 3-carbamoyl-3-hydroxy-4-halobutyric acid with cyanide ions and with alkaline earth metal hydroxide, preferably in the ratio of from about one to about two gram-atoms of calcium and one gram-mol of cyanide (CN)⁻ per gram-mol of 3-carbamoyl-3-hydroxy-4-halobutyric acid, that 3-carbamoyl-3-hydroxy-4-halobutyric acid is preferably obtained by hydrolysis of a 3-cyano-3-hydroxy-4-halobutyric acid in an acidic system (in the presence of cyanide ions), that 3-cyano-3-hydroxy-4-halobutyric acid is preferably obtained by the hydrocyanation of 3-oxo-4-halobutyric acid with HCN in an aqueous system in the presence of excess cyanide ions and preferably in the presence of alkaline earth metal cyanide or alkali metal cyanide, that 3-oxo-4-halobutyric acid is obtained by hydrolysis of a 3-oxo-4-halobutyryl halide produced from diketene by halogenation. Preferred halogens involved in the process are chlorine and, to a lesser extent, bromine. Preferred alkaline earth metal adducts of the present invention are compounds of calcium. A preferred ratio of gram-atoms of calcium to gram-mols of 3-carbamoyl-3-hydroxy-4-chlorobutyric acid is about 2:1.

22 Claims, 5 Drawing Figures

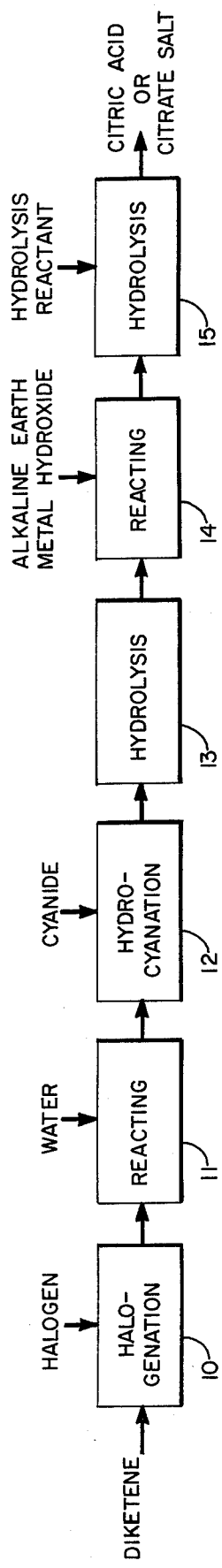
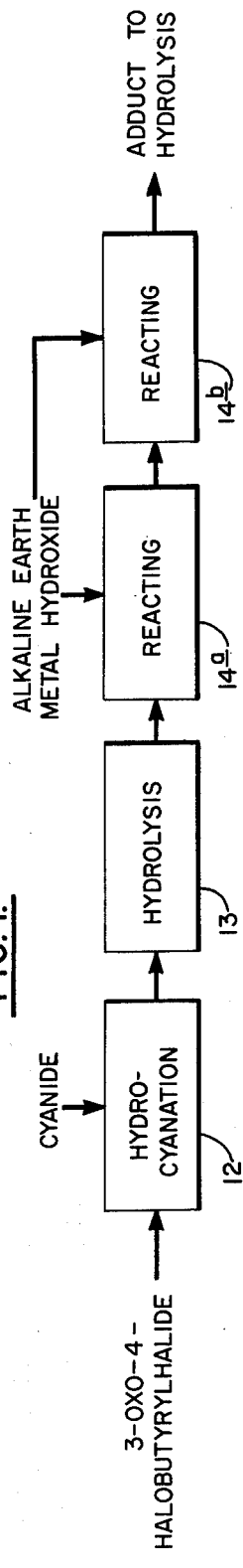
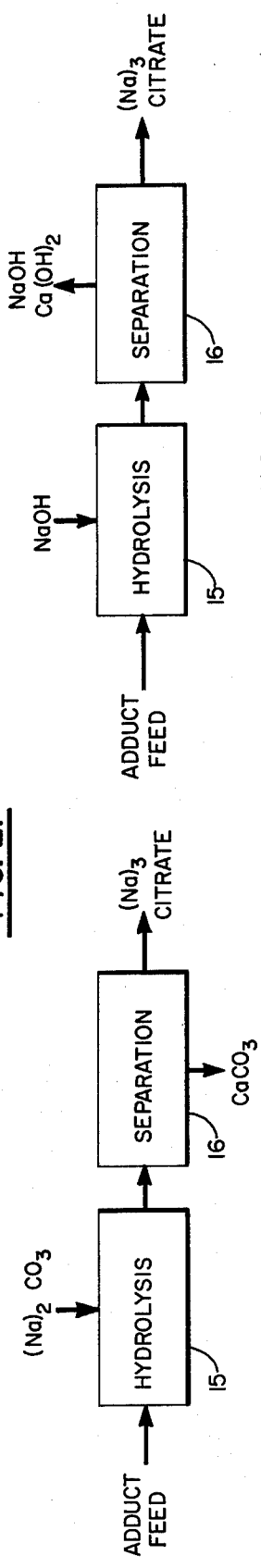

CHEMICAL PROCESS FOR PRODUCING CITRIC ACID

CROSS-REFERENCE TO RELATED APPLICATION

This application is a continuation-in-part of application Ser. No. 172,627, filed Aug. 18, 1971, now U.S. Pat. No. 3,769,337.

BACKGROUND OF THE INVENTION

1. Field of the Invention

The invention relates to the preparation of citric acid and salts of citric acid.

2. Description of the Prior Art

Citric acid or its salts are useful in different ways as exemplified by the following patents: As a plasticizer, U.S. Pat. No. 2,409,703; as a bleaching agent, U.S. Pat. No. 2,529,831; as a food antioxidant, U.S. Pat. No. 2,563,855; as a detergent component, U.S. Pat. No. 2,765,280.

The principal prior sources of citric acid and its derivatives are recovery from natural products such as citrus fruits, and production via micological or fermentation processes. The recovery of citric acid from natural products or sources is disclosed in U.S. Pat. Nos. 2,027,264; 2,193,904; and 2,396,115. The production of citric acid by micological processes is disclosed in U.S. Pat. Nos. 2,353,771; 2,739,923; 2,883,329; and 3,335,067.

Heretofore, the chemical synthesis of citric acid and its salts has proved to be very difficult. In fact, the only known U.S. Pat. No. relating to a chemical synthesis of citric acid is 3,356,721 which issued in 1967 and there is nothing in the patent to show that a significant yield of citric acid or its salts is obtained with the process described therein. Since the amount of natural source citrate is limited, there has been a need in the art for a commercially feasible chemical synthesis process for producing citric acid or its salts.

It is an object of the present invention to provide a process for synthesizing citric acid and salts of citric acid from readily available moderate cost raw materials.

Another object of the present invention is to provide process operations for producing new compositions which are useful intermediates for the synthesis of citric acid and salts of citric acid.

Another object of the present invention is to provide a process for producing intermediate compositions that can be hydrolyzed to produce citric acid or its salts in high yield.

Another object of the present invention is to provide a process for producing intermediate compositions of the preceding objects via a reaction of 3-carbamoyl-3-hydroxy-4-halobutyric acid with cyanide and with alkaline earth metal hydroxide in an aqueous system.

Another object of the present invention is to provide a process for producing 3-carbamoyl-3-hydroxy-4-chlorobutyric acid and for converting that acid to another intermediate useful in the production of citrate wherein it is unnecessary to purify the 3-carbamoyl-3-hydroxy-4-chlorobutyric acid to remove excess cyanide and other impurities associated with the production thereof prior to the conversion.

Another object of the present invention is to provide a process for producing soluble or insoluble alkaline earth metal adduct intermediates which are hydrolyzable to citrate by reaction with acid or base and which process provides inherent self-control of pH in a preferred range for optimum conversion.

Other and further objects and features of the present invention will become apparent upon a careful consideration of the following discussion and the accompanying drawings.

BRIEF DESCRIPTION OF THE FIGURES

FIG. 1 shows in block form a preferred embodiment of the features of the present invention whereby citric acid or its salts are produced from diketene via a sequence involving several novel reactions which provide ways to produce and to utilize the several intermediate compositions involved in the overall process.

FIG. 2 illustrates a process for converting 3-carbamoyl-3-hydroxy-4-halobutyric acid to a calcium adduct readily hydrolyzable to citrate.

FIG. 3 indicates a process for adduct hydrolysis wherein adduct is reacted with alkali-metal carbonate, typically sodium carbonate or potassium carbonate, to produce citrate in the alkali-metal salt form and producing alkaline earth metal carbonate as a by-product.

FIG. 4 indicates a process for adduct hydrolysis wherein adduct is reacted with alkali metal hydroxide (or oxide) to produce citrate in the alkali metal salt form and producing alkaline earth metal hydroxide as a by-product. Usually an excess of alkali metal hydroxide is used; thus the alkaline earth metal hydroxide is usually obtained in admixture with alkali metal hydroxide and the mixture is recycled to the reacting step 14 of FIG. 1.

FIG. 5 indicates additional detail of processing subsequent to the reacting step 14 showing the recycle of alkali metal or alkaline earth metal hydroxide to the reacting step 14.

SUMMARY OF THE INVENTION

The present invention provides a method of producing citric acid and its salts from 3-oxo-4-halobutyric acid wherein close external measurement and control of pH is not a critically difficult matter, the system being largely self-controlling, and wherein several of the numerous reaction steps and stages involved in the overall process are combined so as to occur more or less concurrently.

In accordance with one embodiment of this invention 3-oxo-4-chlorobutyric acid which is obtained by the halogenation of diketene and the subsequent hydrolysis of the halogenation product, is reacted in an aqueous system with an excess of hydrogen cyanide. Preferably, this reaction is carried out in the presence of a small quantity of an alkali metal or an alkaline earth metal compound and with an acidic pH, preferably of from about 1 to about 3. The hydrocyanation reaction occurs rapidly and to a high degree of completion under such conditions producing an aqueous system containing 3-cyano-3-hydroxy-4-chlorobutyric acid, hydrogen cyanide, and residual alkali metal or alkaline earth metal compound. Of course, one should be careful when using systems containing hydrogen cyanide to avoid the polymerization thereof, particularly at temperatures of 50°C and higher.

Without requiring purification of 3-cyano-3-hydroxy-4-butyric acid system or the removal of the cyanide radicals, the system is then reacted with alkaline earth metal hydroxide, the preferred ratio of gram-atoms of alkaline earth metal to gram-mols of 3-carbamoyl-3-hydroxy-4-chlorobutyric acid being about 2:1. Higher ratios than 2:1 are suitable despite the fact that subsequent recovery of the excess alkaline earth metal reactant is usually required.

Under appropriate conditions hereinafter described in greater detail, lesser amounts of alkaline earth metal reactant ranging down to about 1 gram-atom of alkaline earth metal hydroxide per gram-mol of 3-carbamoyl-3-hydroxy-4-chlorobutyric acid may be employed, particularly when subsequent hydrolysis of the intermediate is in an acid system. Where the ratio of gram-atoms of alkaline earth metal hydroxide to gram-mols of 3-carbamoyl-3-hydroxy-4-chlorobutyric acid is 1.5 or lower, it is usually preferred to have co-present up to about 2 gram-atoms of alkali metal hydroxide.

Within the foregoing framework of ratios of alkaline earth metal hydroxide and alkali metal hydroxide per molecule of 3-carbamoyl-3-hydroxy-4-chlorobutyric acid, one obtains either an insoluble adduct or a soluble adduct depending on the proportions and mode of operation. In general, the insoluble adducts are preferred as are the proportions and constituents which produce them because of the ease with which an insoluble material may be recovered from impurities, by-products and excess reactants.

The soluble and the insoluble adducts are readily hydrolyzed in either a basic or an acidic environment to produce a citrate, the term citrate being used to denote a compound containing the structure:

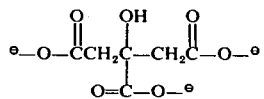

either in solution or as a substantially solid or particulate material containing hydrogen, alkali metal or alkaline earth metal linked at the ionically indicated points. Where the hydrolysis is in an acidic environment, the citrate product is citric acid. Where the hydrolysis is in a basic environment, the citrate product is a salt of citric acid, the metal constituency of such salt being that of the basic material used in hydrolysis. Typically, where the hydrolysis is with an alkali metal hydroxide such as sodium hydroxide or potassium hydroxide, the citric acid salt is sodium citrate or potassium citrate, respectively. Typically, where the hydrolysis is with an alkaline earth metal hydroxide, the citrate salt is an alkaline earth metal salt; for example, barium hydride yields a barium salt.

One of the outstanding advantages of the foregoing processing wherein 3-carbamoyl-3-hydroxy-4-halobutyric acid is reacted with cyanide and with alkaline earth metal hydroxide stems from the fact that the system is virtually self-controlling with respect to pH which is known to be critical and difficult to control in many systems or processes to bring about an orderly progression through a sequence of several reactions. Generally speaking, the first of these reactions is a reaction of the starting acid wherein one gram-mol of 3-carbamoyl-3-hydroxy-4-halobutyric acid reacts with one-half gram-atom of alkaline earth metal to produce a salt of the acid, liberating water. Although this reaction can be conducted independently in one stage and the salt produced used for feed to a subsequent stage for the next reaction by providing only the one-half gram-atom of alkaline earth metal per gram-mol of 3-carbamoyl-3-hydroxy-4-halobutyric acid at first, the balance if any being added later, usually this represents undesired and unnecessary complications and it is preferred that a greater amount of alkaline earth metal hydroxide be available at the outset, preferably up to the entire 2 gram-atoms thereof per gram-mol of 3-carbamoyl-3-hydroxy-4-halobutyric acid.

With additional alkaline earth metal hydroxide available beyond that necessary to convert the starting 3-carbamoyl-3-hydroxy-4-halobutyric acid to the salt, a second one-half gram-atom of alkaline earth metal per gram-mol of 3-carbamoyl-3-hydroxy-4-halobutyrate fed reacts with the halogen atom present forming by-product alkaline earth metal halide and bringing about the epoxidation of the 3-carbamoyl-3-hydroxy-4-halobutyric acid salt to produce a 3-carbamoyl-3,4-epoxybutyric acid salt.

With sufficient alkaline earth metal present in the system, and with cyanide ions present, a basic cyanide condition exists in the system which causes a third reaction to occur. This third reaction is a cleavage of the epoxide ring produced in the second reaction thereby forming a 3-carbamoyl-3-hydroxy-4-cyanobutyric acid salt of the alkaline earth metal of the system. This reaction is usually much slower than the virtually instantaneous epoxidation reaction.

Although lesser quantities of available base or metal cations may be present in the system at this point, it is usually preferred that at least one gram-atom of available alkaline earth metal be present in the system for this reactor; i.e., in addition to the amount involved in the preceding dehalogenation and salt formation.

The material produced at this point with a typical overall feed of 2 gram-atoms of alkaline earth metal has the characteristics of an insoluble adduct citrate precursor containing up to about 1.5 gram-atoms of alkaline earth metal per gram-mol of 3-carbamoyl-3-hydroxy-4-halobutyric acid fed. Apparently this reaction goes through an intermediate stage of 3-hydroxy-3,4-dicarbamoylbutyric acid salt which is soluble and which readily undergoes further hydrolysis to the insoluble species. In most cases, the adduct is initially a water soluble adduct where the reaction has been conducted with less than 2 gram-atoms of alkaline earth metal present per gram-mol of 3-carbamoyl-3-hydroxy-4-halobutyric acid fed. The soluble state generally prevails until the system is heated to drive off ammonia. As the reaction is carried out where 2 gram-atoms of alkaline earth metal are present, or with 1.5 gram-atoms of alkaline earth metal and one gram-atom of alkali metal present, the latter system being heated to remove ammonia, the insoluble adduct forms much more readily. The water insoluble adduct of the systems described readily precipitates and is recovered from the balance of the system in high purity (90 percent or better) by simple separation operations such as filtration or centrifuging.

The purification advantages provided by the separation of an insoluble precipitate at this point make highly preferable such embodiments. Either of the insoluble or the soluble adducts is readily hydrolyzed to a citrate of either acid or salt form by hydrolysis with either a strong acid or strong base.

From the foregoing brief description, it is apparent that many of the principal reaction steps described, particularly those of the preferred arrangement, can be conducted in a single reactor in a batchwise, continuous or semi-continuous manner by feeding all of the required reactants including the 3-carbamoyl-3- hydroxy-4-halobutyric acid, the cyanide, and the alkaline earth metal hydroxide. Alternately the various intermediates may be produced and utilized separately in two or more steps.

It is to be understood that, although the reactions are described as involving a reaction of alkaline earth metal hydroxide, the required alkaline earth metal hydroxide "reactant" may be obtained in various ways. For example, alkaline earth metal oxide may be mixed with water in a separate vessel to form a hydroxide solution which is combined with the 3-carbamoyl-3-hydroxy-4-halobutyric acid and hydrogen cyanide system resulting from the previous reactions as described. Alternatively, the required alkaline earth metal hydroxide is obtained by merely adding alkaline earth metal oxide to the aqueous system of 3-carbamoyl-3-hydroxy-4-halobutyric acid and hydrogen cyanide resulting from the prior reactions.

The operation of adding alkaline earth metal oxide to an aqueous system is a well-known process of "slaking" where the alkaline earth metal is calcium. This reaction is exothermic, thus, it is preferred to form the alkaline earth metal hydroxide in a separate system provided with appropriate cooling.

Although it is usually preferred to employ about 2 gram-atoms of alkaline earth metal hydroxide per gram-mol of 3-carbamoyl-3-hydroxy-4-chlorobutyric acid so as to produce an insoluble alkaline earth metal adduct and by-product inorganic alkaline earth metal halide salt, alkali metal may be substituted for part of the alkaline earth metal requirements provided at least one gram-atom of alkaline earth metal is used in the system per gram-mol of 3-carbamoyl-3-hydroxy-4-halobutyric acid used. Thus a typical mixed system uses about 1.5 gram-atoms of calcium and about one gram-atom of sodium per gram-mol of 3-carbamoyl-3-hydroxy-4-halobuyric acid.

The alkaline earth metal adduct produced by the foregoing reactions is hydrolyzed with acid or base to form citrate. Preferably, to minimize reaction times, strong acid or strong base is employed for the hydrolysis. Typical acid is hydrochloric acid whereas typical base is alkali metal hydroxide such as sodium hydroxide or potassium hydroxide. The feed of sodium or potassium hydroxide in basic hydrolysis produces soluble sodium or potassium citrate. Removal of alkaline earth metal is facilitated by feeding an alkali metal carbonate in hydrolysis with or without feeding additional alkali metal hydroxide as such or as an oxide. The carbonate ions produce poorly soluble alkaline earth metal carbonate easily removed from the system.

The foregoing process sequence may be represented by the following series of equations:

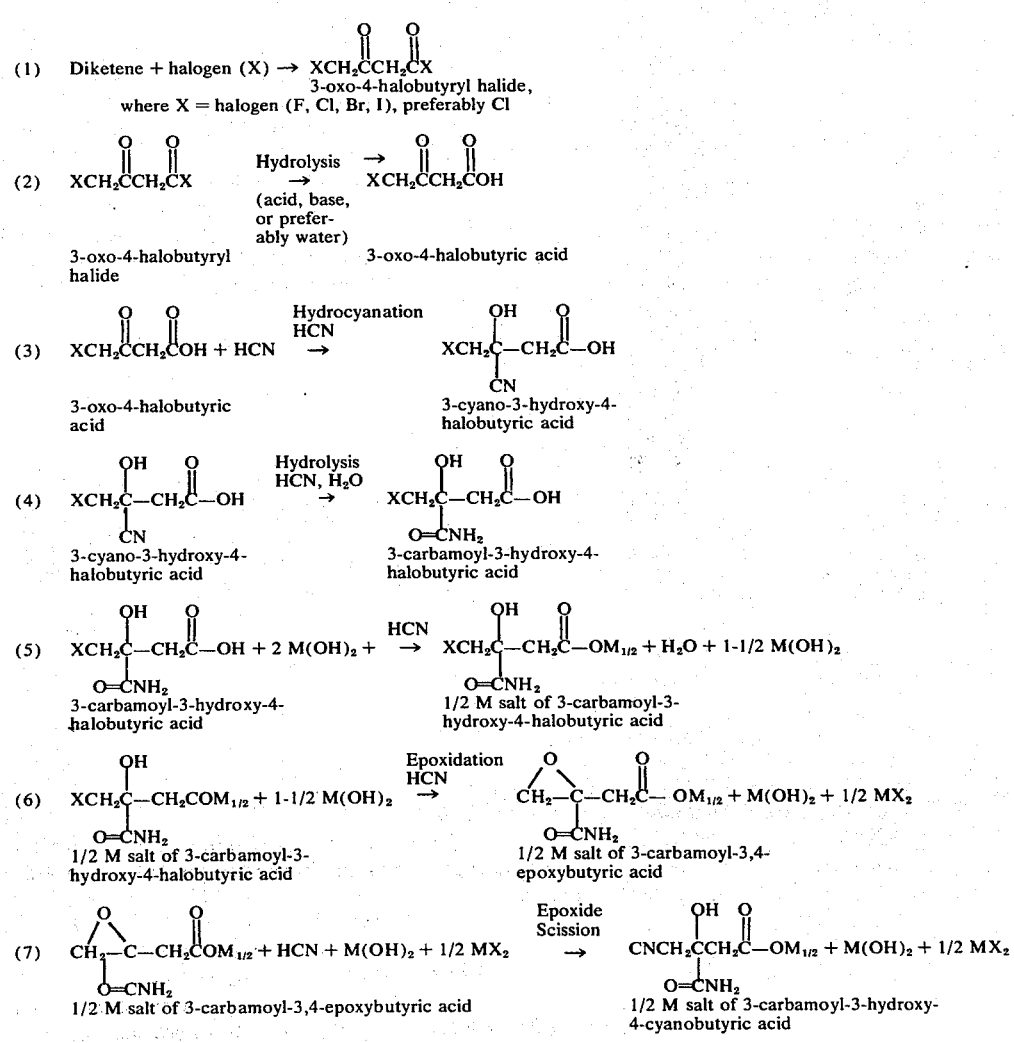

(8) 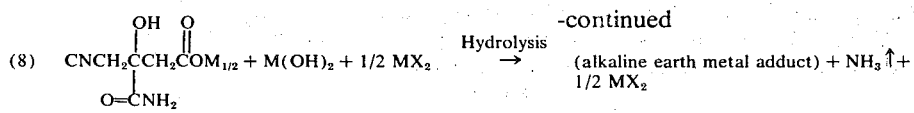 →(Hydrolysis) (alkaline earth metal adduct) + NH$_3$↑ + 1/2 MX$_2$ (9a) (alkaline earth metal adduct) + excess HCl → citric acid + MCl$_2$ (9b) (alkaline earth metal adduct) + excess KOH → 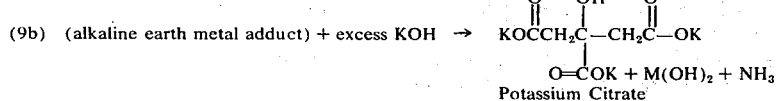 + M(OH)$_2$ + NH$_3$
Potassium Citrate (9c) (alkaline earth metal adduct) + 1-1/2 NaCO$_3$ → 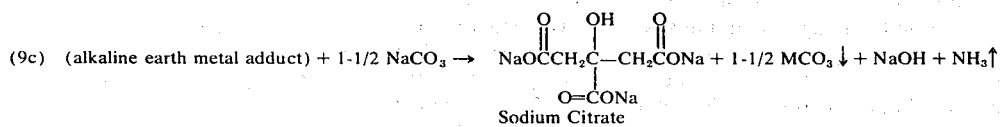 + 1-1/2 MCO$_3$↓ + NaOH + NH$_3$↑
Sodium Citrate The foregoing equations imply the equilibrium between M(OH)$_2$ and 2HCN on one side and M(CN)$_2$ and 2H$_2$O on the other. Also in the equations, the term M means alkaline earth metal ion (Be$^{++}$, Mg$^{++}$, Ca$^{++}$, Sr$^{++}$, Ba$^{++}$). A preferred alkaline earth metal ion is Ca$^{++}$.

The foregoing process is subject to numerous variations. Thus, although the reactions are preferably conducted in an aqueous environment or in aqueus solutions, it is possible to employ suitable anhydrous organic reaction media including protic solvents such as alcohols and alcohol/water mixtures in at least some of the reactions alone or in combination with water. In some instances, esters are used to facilitate handling and the selection of solvent systems. Although the process is most preferably conducted on a continuous basis in an unbroken sequence in one or more reactors, it is feasible to perform the process on a batch or a semi-batch basis and also to interrupt the processing sequence operations, e.g. by storing or transporting intermediates for subsequent use in the succeeding process steps. Thus the process typically begins with diketene and proceeds through the steps shown. In other instances it is desired to start with ketene and produce diketene as a first step. In still other instances it is desired to start with acetic acid or acetone which is pyrolyzed in accordance with known processes to provide ketene, the latter in turn being reacted to diketene. In addition, as noted previously, in many instances several reactions described are preferably conducted concurrently or sequentially in a single environment to appear as a single processing step. On the other hand, single reactions may be conducted in a staged manner in several reaction vessels or systems.

Inasmuch as this process is subject to numerous variations, the following are some of the process embodiments disclosed or provided by this invention.

A. Reacting 3-carbamoyl-3-hydroxy-4-halobutyric acid in an aqueous system in the presence of cyanide ions with a sufficient quantity of alkaline earth metal hydroxide to form an alkaline earth metal adduct and subjecting said adduct to hydrolysis under alkaline or basic conditions to form a citrate. Preferred proportions are about 1 mol of cyanide radicals (CN)$^-$ and 2 gram-atoms of alkaline earth metal (calcium) per gram-mol of 3-carbamoyl-3-hydroxy-4-halobutyric acid to produce an alkaline earth metal adduct readily hydrolyzable to citric acid or a salt of citric acid using acidic or basic hydrolysis conditions.

B. Reacting 3-oxo-4-chlorobutyric acid with at least about 2 gram-mols of HCN per gram-mol of 3-oxo-4-chlorobutyric acid in an aqueous system in the presence of alkali metal cyanide or alkaline earth metal cyanide to form a mixture containing hydrogen cyanide and 3-cyano-3-hydroxy-4-chlorobutyric acid in at least about a 1:1 molar ratio, hydrolyzing the 3-cyano-3-hydroxy-4-chlorobutyric acid system with water at a pH of from about 1.0 to about 3.0 to form a system containing hydrogen cyanide and 3-carbamoyl-3-hydroxy-4-chlorobutyric acid; reacting 3-carbamoyl-3-hydroxy-4-chlorobutyric acid in an aqueous system with about 1 gram-mol of cyanide and at least one gram-atom of alkaline earth metal hydroxide per gram-mol of 3-carbamoyl-3-hydroxy-4-chlorobutyric acid to form an alkaline earth metal adduct, and reacting said adduct with alkali metal hydroxide, oxide or carbonate or with mineral acid to produce alkali metal citrate or citric acid.

C. In addition, alkaline earth metal or mixtures of alkaline earth metal and alkali metal hydroxide may be used in various proportions as long as at least 1 gram-atom of alkaline earth metal is used per gram-mol of 3-carbamoyl-3-hydroxy-4-halobutyrate

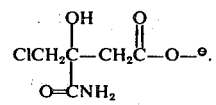

Typical proportions of gram-atoms of alkaline earth metal hydroxide AEMH and alkali metal hydroxide AMH per gram-mol of 3-carbamoyl-3-hydroxy-4-chlorobutyrate are as follows:

| AEMH | gram atoms AMH |
|---|---|
| 1 | 2 |
| 1 | 1 |
| 1.5 | 0.5 |
| 1.5 | 0 |
| 1.5 | 1 |
| 2 | 0 |

The systems in the region of the first four proportions typified in the foregoing table produce soluble alkaline earth metal adducts unless they are heated vigorously (60°–100°C) or allowed to stand for a substantial period of time releasing ammonia. The systems produced in the latter two proportions regions indicated in the foregoing produce insoluble alkaline earth adducts even without the vigorous heating or long duration standing.

D. Reacting 3-oxo-4-chlorobutyric acid with HCN in an aqueous system to form 3-cyano-3-hydroxy-4-chlorobutyric acid, reacting 3-cyano-3-hydroxy-4-chlorobutyric acid with water at a pH of from about 1.0 to about 3.0 to form 3-carbamoyl-3-hydroxy-4-chlorobutyric acid, reacting 3-carbamoyl-3-hydroxy-4-chlorobutyric acid in an aqueous system with about 1 gram-mol of cyanide $(CN)^-$ and at least about 1.0 gram-mol of alkaline earth metal hydroxide per gram mol of 3-carbamoyl-3-hydroxy-4-chlorobutyric acid to form an alkaline earth metal adduct, and reacting said adduct with alkali metal hydroxide, oxide or carbonate or with mineral acid to produce alkali metal citrate or citric acid.

E. Forming an aqueous solution containing 3-carbamoyl-3-hydroxy-4-halobutyrate ions, cyanide ions and alkaline earth metal ions, and reacting said system at a temperature from about 0° to about 100°C to produce an alkaline earth metal adduct hydrolyzable to citric acid or its salts.

It can be seen from the foregoing that numerous new and highly useful intermediates are formed in the above process. Accordingly, this invention also provides as new compositions the following:

I. The adduct produced by reacting an alkaline earth metal salt of 3-carbamoyl-3-hydroxy-4-halobutyric acid with alkaline earth metal hydroxide in proportions of from about 0.5 to about 2 gram-mols of hydroxide per gram-mol of salt of 3-carbamoyl-3-hydroxy-4-halobutyric acid.

DETAILED DESCRIPTION OF THE INVENTION

In a preferred embodiment of the present invention, a preferred starting material is 3-oxo-4-chlorobutyryl chloride, preferred because of the excellent properties of the chlorine compounds in the reactions described herein as well as because of low cost and ease of formation initially. This material is readily obtained by chlorination of diketene, in a reaction that proceeds readily at temperatures of from about −20°C to about 30°C. Preferably, the chlorination is conducted in a halogenated hydrocarbon diluent such as carbon tetrachloride, ethylene dibromide, ethylene dichloride, methylene dichloride, fluoro-chloro methanes or ethanes. Preferred diluents are fully halogenated compounds which do not undergo further halogenation in the reaction system. For further details on the halogenation reaction, reference may be had to U.S. Pat. No. 2,209,683. A preferred diluent is carbon tetrachloride.

The 3-oxo-4-halobutyryl halide is converted into 3-oxo-4-halobutyric acid by reaction with water in a hydrolysis reaction preferably in the presence of diluent remaining from chlorination. Surprisingly, this reaction proceeds quantitatively and at a high rate. Preferably, it is conducted by adding hydrolyzing reactant, typically water, to the diluent containing solution carried through from the prior halogenation reaction. The acidic product formed at this point is not soluble in the diluent systems described so that it readily precipitates and can be recovered in high purity by filtration, centrifuging and the like. Recovered diluent can be recycled.

Another product of the hydrolysis of 3-oxo-4-chlorobutyryl chloride is hydrogen chloride, which evolves as a vapor during the hydrolysis. In some instances the removal of hydrogen halide is facilitated by the use of a suitable inert stripping gas such as nitrogen, oxygen, air, carbon dioxide, steam, and the like. The diluent and the product acid are readily separated for further processing of the acid and recycle of the diluent. There is thus obtained intermediate 3-oxo-4-chlorobutyric acid in high purity and in excellent yield of the order of 90–95 percent based on the diketene starting material. The hydrolysis occurs readily in virtually 100 percent yield at ordinary room temperature, broadly at temperatures of from about 0° to about 50°C using a 25 percent solution of the 3-oxo-4-halobutyryl chloride in carbon tetrachloride, carbon disulfide or ethylene dichloride solvent. Water for hydrolysis is fed to the system in about stoichiometric proportions of one mol of water per mol of 3-oxo-4-chlorobutyryl halide. Although different proportions ranging up to about a 100 percent excess of either reactant may be used, it is preferred to use about stoichiometric proportions.

The 3-oxo-4-chlorobutyric acid thus obtained is reacted with cyanide to convert the 3-oxo-group to a cyanohydrin structure. This reaction proceeds readily with HCN, preferably in a system containing an excess of HCN, ranging from about stoichiometric up to about three equivalents of excess cyanide radicals per mol of 3-oxo-4-chlorobutyric acid. Typically, the reaction is in the presence of from about 0.001 to about 1.0 gram-mol of alkali metal cyanide or from about 0.0005 to about 0.5 gram-mol of alkaline earth metal cyanide per gram-mol of 3-oxo-4-chlorobutyric acid. Typically, the alkali metal or alkaline earth metal cyanide is fed as such or is, in effect, generated in situ by feeding precursor materials such as sodium, potassium or calcium hydroxide or oxide in addition to the HCN. A typical specific ratio is about 0.1 gram-atom of alkali metal or 0.05 gram-atom of alkaline earth metal per gram-mol of cyanide radical $(CN)^-$ present. Preferably, HCN or a mixture of HCN and NaCN is the source of cyanide radicals and cyanide radicals are fed in proportions of about 2.0–2.5 gram-mols of cyanide $(CN)^-$ per gram-mol of 3-oxo-4-chlorobutyric acid. Higher proportions of cyanide are permissible; however, where more than stoichiometric amounts are used, provision for recovery and recycle of the excess is necessary and the problem of polymerization of HCN becomes more significant. Typically, the reaction proceeds in from about one-quarter to about 10 hours at a temperature of from about 0 to about 50°C with about 2 gram-atoms of cyanide per gram-mol of 3oxo-4-chlorobutyric acid. The yield of 3-cyano-3-hydroxy-4-chlorobutyric acid is substantially stoichiometric.

At this point the 3-cyano-3-hydroxy-4-chlorobutyric acid containing, typically, about one excess cyanide radical per molecule of 3-cyano-3-hydroxy-4-chlorobutyric acid, is subjected to a hydrolysis reaction wherein the 3-cyano group is converted to a 3-carbamoyl group to produce 3-hydroxy-3-carbamoyl-4-chlorobutyric acid. The hydrolysis is conducted in an acidic system at a pH of from about 0.5 to about 6.0, preferably 1.0 to 3.0, for a time of from about 15 minutes to about 10 hours and at a temperature of from about 0° to about 60°C. Usually, this hydrolysis is partly concurrent with the preceding cyanohydrination reaction and is concluded in a higher temperature extension of the cyanohydrination, usually at least 10°C higher than the preceding reaction. Particularly preferred pH for this hydrolysis reaction is from about 1.0 to about 2.5, typically about 2.0, which is normally readily provided by the organic acid in this system without requiring the addition of stronger acids. Where more than about 5.0 wt. percent of alkali metal or alkaline earth metal cyanide is used in the cyanohydrination, pH will tend to be in the region of 2.0–2.7 or higher. Where the pH is higher (more alkaline) than desirable, it is usually preferred to acidify the system to produce the desired pH of from about 1.0 to about 2.5 by the addition of an appropriate amount of strong mineral acid such as HCl or $H_2SO_4$. The addition of such strong acid usually results in the formation of a salt of the alkali metal or alkaline earth metal present and of the strong acid.

Typical yields for the process cyanohydrination and hydrolysis which produces 3-carbamoyl-3-hydroxy-4-chlorobutyric acid from 3-oxo-4-chlorobutyric acid are about 95 percent.

The 3-carbamoyl-3-hydroxy-4-chlorobutyric acid system from the preceding step usually contains excess cyanide (HCN) plus residual alkali metal or alkaline earth metal cyanide or salt; viz, sodium cyanide, or sodium chloride. Usually the excess HCN is present because an excess is deliberately used in the hydrocyanation reaction; however, the system may be subjected to purification if desired to remove the excess HCN and the salt. Although such purification has advantages in connection with storage and transportation of the 3-carbamoyl-3-hydroxy-4-chlorobutyric acid, it is generally preferred that the expense and inconvenience of separation be avoided and that the mixed acid, salt and cyanide system be reacted directly with an alkaline earth metal hydroxide in an aqueous system.

Several reactions occur, forming quite rapidly a 3-carbamoyl-3,4epoxybutyrate system. This operation is typically conducted in the presence of about two grammols of calcium fed as the oxide or hydroxide per gram-mol of 3-carbamoyl-3-hydroxy-4-chlorobutyric acid and at a temperature of from about 0° to about 50°C for a period of time from about 5 minutes to about 6 hours. Several reactions occur in the operation; viz, a calcium salt of 3-carbamoyl-3-hydroxy-4-chlorobutyric acid is formed together with calcium cyanide, the chlorine of the 3-carbamoyl-3-hydroxy-4-chlorobutyric acid salt reacts with part of the calcium present to form one-half gram-mol of by-product calcium chloride per gram-mol of 3-carbamoyl-3-hydroxy-4-chlorobutyric acid fed, the epoxidation occurs, and a cleavage of the epoxide begins to form 3-carbamoyl-3-hydroxy-4-cyanobutyrate salt.

The alkaline earth metal hydroxide is usually provided for the reaction by feeding an alkaline earth metal oxide directly to the aqueous 3-carbamoyl-3-hydroxy-4-chlorobutyric acid system or, preferably, by producing separately a hydroxide solution or slurry of alkaline earth metal oxide, hydroxide and water and feeding such to the reaction system.

It appears that the epoxidation reaction occurs rapidly as the halogen is eliminated in the formation of alkaline earth metal halide and that this fast reaction is followed by a comparatively slow epoxide cleavage reaction which converts the 3,4-epoxy-structure into a 3-hydroxy, 4-cyano structure.

The conversion of the 4-cyano group to a carboxylic acid group is then brought about by hydrolysis. Preferably, this is done in several stages, the first of which is virtually a continuation of the preceding stage, usually at somewhat higher temperature.

Preferably, the reactants are proportioned in accordance with the foregoing discussion and reacted for a sufficient time to liberate ammonia, to produce an insoluble calcium precipitate which is readily recovered in a good purity stage by filtration or centrifuging wherein the by-product calcium chloride, as well as other by-products such as calcium acetate and ammonia, are separated from the insoluble precipitate. In this hydrolysis it appears that a soluble 3-hydroxy-3,4-dicarbamoylbutyrate intermediate is formed at an early stage and that it in turn is converted to an insoluble adduct, particularly as ammonia is evolved and permitted to escape. This hydrolysis is typically conducted at a temperature of from about 50° to about 150°C for a time from about 15 minutes to about 6 hours. A preferred time is about 1½ hours at a temperature of about 90°C. Although less preferred, the adduct can be obtained as a soluble adduct and subjected to the next step.

The recovered calcium adduct produced in the preceding operation, preferably an insoluble adduct which has precipitated from solution that has been separated from the resulting solution is subjected to hydrolysis under alkaline or acidic conditions to form a citrate. Where citric acid is a desired citrate the adduct is usually converted to citric acid via an acidic hydrolysis using a mineral acid, typically HCl. If alkali metal citrate is desired, the citric acid is readily converted to trisodium citrate by reaction with alkali metal hydroxide.

In an alternate hydrolysis procedure, the trisodium salt of citric acid is produced more directly by reacting alkali metal carbonate hydroxide or both with the adduct. The use of a carbonate results in the formation of insoluble calcium carbonate which is readily removed by filtration leaving an aqueous solution of trisodium citrate. Alkali metal hydroxide, is present, can be separated by fractional crystallization. Basic hydrolysis is conducted at a temperature from about room temperature up to about 150°C for a period of time from about 2 hours to about 5 days.

Where it is desired to avoid disposal problems attendant to the production of calcium carbonate in basic hydrolysis, sodium hydroxide is used in an exchange reaction which forms calcium hydroxide and trisodium citrate. It may be necessary to add a small quantity of $Na(CO)_3$ or $CO_3$ to remove small quantities of soluble $Ca(OH)_2$. The calcium hydroxide and excess sodium hydroxide are preferably recovered and recycled to earlier stages in the process. This calcium chloride from the hydrolysis of the 3-carbamoyl-3-hydroxy-4-cyanobutyrate is the only calcium compound by-product for which disposal must be arranged.

The overall yield from 3-carbamoyl-3-hydroxy-4-chlorobutyric acid to the insoluble adduct obtained by the hydrolysis of the 3-carbamoyl-3-hydroxy-4-cyanobutyrate is typically from 90 to 93 percent. The insoluble adduct is readily obtained in better than 90 percent purity. Yields in the hydrolysis of the insoluble adduct producing trisodium citrate via acidic hydrolysis and neutralization with caustic are virtually 100 percent. Yields of trisodium citrate by the basic hydrolysis routes are somewhat lower usually ranging upward from about 80 percent.

AMPLIFIED DESCRIPTION WITH REFERENCE TO FIGURE

With reference now to FIG. 1 of the drawing, the process indicated in block form therein represents a preferred embodiment of the present invention providing a process for producing a citrate product and intermediates useful for producing said product from a comparatively low cost and readily available starting material, diketene. It will be appreciated by those skilled in the art that diketene is obtained readily by pyrolysis of acetic acid or acetone to produce ketene and that ketene is dimerized readily to produce diketene. In the process of FIG. 1 the diketene is reacted at 10 with a halogen, typically chlorine, to produce 3-oxo-4-halobutyryl halide, typically 3-oxo-4-chlorobutyryl chloride.

The 3-oxo-4-halobutyryl halide obtained from halogenation 10 is reacted with water at 11 in a hydrolysis reaction producing 3-oxo-4-halobutyric acid, typically 3-oxo-4-chlorobutyric acid.

At 12, the 3-oxo-4-halobutyric acid is reacted with cyanide ions in an aqueous system, preferably in the presence of alkali metal or alkaline earth metal ions forming 3-cyano-3-hydroxy-4-halobutyric acid. Alternately, for example, 3-cyano-3-hydroxy-4-halobutyric acid is produced by reacting 3-oxo-4-halobutyric acid with an alkali metal cyanide to form an alkali metal salt of 3-cyano-3-hydroxy-4-halobutyric acid following which the salt is converted to the acid by an acidification reaction with a suitable strong acid such as hydrochloric acid.

The 3-cyano-3-hydroxy-4-halobutyric acid produced at 12 is hydrolyzed at 13 to form 3-carbamoyl-3-hydroxy-4-halobutyric acid. Preferably the pH is from about 1.0 to about 3.0.

At 14, 3-carbamoyl-3-hydroxy-4-halobutyric acid is reacted in an aqueous system with alkaline earth metal hydroxide or with a mixture of alkaline earth metal hydroxide and alkali metal hydroxide, with about 1 gram-mol of cyanide $(CN)^-$ and at least about 1 gram-atom of alkaline earth metal available per gram-mol of 3-carbamoyl-3-hydroxy-4-halobutyric acid, to form an adduct. Preferably the adduct is produced as an insoluble precipitate readily recovered for purification purposes by suitable separation operations such as filtration and centrifuging.

The soluble or insoluble adduct obtained at reacting step 14 is hydrolyzed at 15 to produce a citrate product. It will be understood that, although the hydrolysis at 15 is indicated to be in a single step, normally it is preferred to perform this operation in two or more stages usually under somewhat different conditions of temperature in the different stages. Various hydrolysis reactants are suitable for use at hydrolysis 15 depending upon the results desired. In general, it is preferred to use an acid hydrolysis reactant such as hydrochloric acid, sulfuric acid, or other suitable strong acid which upon hydrolysis of the adduct results in the formation of citric acid. On the other hand, where a citrate salt is the desired product, a basic hydrolysis is generally preferred so as to produce the salt directly, the hydrolysis reactant being typically an alkali metal hydroxide.

As noted in the preceding discussion, several reactions occur at 14 and proceed in a more or less concurrent and sequential manner preferably producing an insoluble adduct which is recovered and supplied to hydrolysis 15 for the conversion to citrate. Each of the reacting 14 and the hydrolysis 15 can be conducted in two or more stages under similar or different conditions seeking to optimize reaction rates and conversions, to minimize the formation of by-products, and to obtain other processing advantages.

In general, the preferred alkaline earth metal hydroxide used at 14 is calcium hydroxide obtained either by feeding a calcium hydroxide solution to reacting step 14 or by feeding an alkaline earth metal oxide such as calcium oxide. Where an alkaline earth metal oxide is used, generally it is preferred that the maintenance of uniform conditions and removal of heat be facilitated by combining the calcium oxide with water in a separate vessel producing a calcium hydroxide solution which solution is proportioned as one of the feeds to the reacting step 14.

A preferred hydrolysis reactant at 15 is an alkali metal hydroxide, oxide or carbonate or a mineral acid such as hydrochloric acid. A strong base such as sodium hydroxide or potassium hydroxide or an alkali metal carbonate such as sodium carbonate is usually preferred when a citric acid salt is desired. Thus, generally speaking, the pH at hydrolysis 15 is more acid than about 1.5 or more basic than a pH of about 11.0.

The various reactions involved in the process of FIG. 1 involve temperatures, pH's and times which are important but which are not highly critical. Since in most instances several reactions occur more or less simultaneously or concurrently in the same environment at elevated temperatures for long periods of time, and side reactions are possible, usually it is advantageous to optimize the various steps with regard to conditions and in some instances to perform at least some of the individual steps in two or more stages at different temperatures. One of the important features of the present invention is that the critical aspect of pH is virtually self-controlling.

The halogenation 10 occurs readily at low temperatures of the order of from about −30° up to about +30°C. Since operation at the low temperatures is expensive in terms of the cooling required, normally it is preferred that this halogenation reaction be performed at temperatures of from about +20° to about +30°C. The halogenation reaction is rapid when using about stoichiometric proportions of reactants so that in general it is unnecessary to use large excesses of any reactant to achieve useful reaction rates.

The hydrolysis reaction at 11 is likewise rapid and occurs in good yield at moderate temperatures of the order of 20° to 30°C which temperatures are generally preferred; however, it is also practical to operate at temperatures up to about 50°C to avoid the necessity for refrigeration cooling even under conditions of high ambient temperatures. Similarly, the hydrocyanation reaction 12 occurs readily at temperatures of the order of 25° to 50°C and such temperatures represent preferred conditions for this step.

The hydrolysis 13 preferably is conducted at somewhat higher temperatures than the preceding hydrocyanation.

Reacting 14, as previously noted, involves several different reactions including formation of a salt, epoxidation, and cleavage of the epoxide. The first two reactions of these three occur rapidly even at moderate temperatures of the order of 25° to 50°C so that in general it is unnecessary to use higher temperatures for this part of the reaction. The third reaction of the sequence, viz, the cleavage of the epoxide, is a comparatively slow reaction which generally benefits from the use of somewhat higher temperatures ranging up to about 75°C. Thus, it is usually preferred that the reacting 14 be performed in at least two different stages, a first of which is at temperatures of the order of 25° to 50°C while the second stage of the step 14 is conducted in a larger vessel for longer times at somewhat higher temperatures up to about 100°C but usually preferably below 75°C.

Similarly, the hydrolysis 15 appears to involve several different reactions, some of which proceed at a satisfactory rate at moderate temperatures of the order of 25° to 50°C in fairly short times of the order of several hours, while the concluding reactions generally are conducted at much higher temperatures ranging from about 75° to 150°C and preferably are conducted for prolonged periods of time of the order of 4 or more hours. Thus the hydrolysis step 15 also usually is conducted in a staged manner involving at least two stages. It will be appreciated that where the hydrolysis 15 is with acid to produce citric acid and wherein the desired product is a citrate salt, an acid hydrolysis is followed by a neutralization reaction with suitable base to produce the desired salt. In a typical situation where the desired salt is the sodium salt of citric acid, the neutralization is typically with sodium hydroxide. Similarly, the use of other hydroxides results in the production of potassium citrate, lithium citrate, calcium citrate and the like.

With reference not to FIG. 2 of the drawing, the apparatus shown therein indicates a portion of the process of FIG. 1 wherein the hydrocyanation step 12 and the hydrolysis step 13 are similar to corresponding steps in FIG. 1 and wherein the reacting step 14 is shown as two separate stages 14a and 14b. For illustrative purposes, about half of the alkaline earth metal hydroxide (one gram-atom of alkaline earth metal per gram-mol of 3-oxo-4-halobutyryl halide) is fed at 14a and the balance of the alkaline earth metal ions, if any, are fed at 14b.

FIG. 3 indicates a hydrolysis operation useful in FIG. 1 or in conjunction with FIG. 2 wherein the adduct from the reacting step 14 or 14b is fed to a hydrolysis step indicated by reference character 15 to which also is fed an alkali metal carbonate such as sodium carbonate. The feed of such a carbonate results in the formation of calcium carbonate and alkali metal citrate, typically sodium citrate. Separation at this point such as by filtration or centrifuging removes the insoluble calcium carbonate leaving a solution of sodium citrate from which water is removed to provide solid sodium citrate. In a typical process, the sodium citrate is recovered from the solution by evaporation to produce particulate sodium citrate in a mother liquor and the mother liquor is removed by filtration or centrifuging.

FIG. 4 indicates an alternate hydrolysis and recovery arrangement wherein the hydrolysis 15 is conducted with alkali metal hydroxide, usually in excess, resulting in the formation of a hydrolysis product containing alkaline earth metal hydroxide.

The separation 16 for such a system is preferably a fractional crystallization recovering in addition to the sodium citrate, a mixture of excess alkali metal hydroxide and alkaline earth metal hydroxide, the latter hydroxide solution being recovered and recycled to either or both of the reacting steps 14a and 14b of FIG. 2 or to the reacting step 14 of FIG. 1. It is by such a feed of a mixture of alkali metal hydroxide and alkaline earth metal hydroxide that one comes to the point of considering the adduct solubility aspects previously tabulated for typical proportions involving mixed alkali metal and alkaline earth metal systems.

The advantages of forming the insoluble adducts at the reacting step 14 or 14a and 14b are so great with regard to recovering an intermediate or adduct of high purity and facilitating the removal of impurity material such as residual reactants, by-products and the like, that a preferred embodiment of the process of the present invention places a distinct separation step between the reacting step 14 and the hydrolysis 15 as shown in FIG. 5. With such a distinct recovery step 17, a mother liquor is produced thereby containing among other things excess hydroxide reactant. Typically, at least a part of this mother liquor recovered from step 17 is recycled to either or both of the reacting steps 14a or 14b of FIG. 2 or to reacting 14, generally, of FIG. 1 and FIG. 5. Such a recycle is indicated in FIG. 5 by the line 18.

From the foregoing, it is evident that various types of hydroxide and citrate recycle streams can be handled to advantage and that some streams may be merely combined or applied separately. As an example, the hydroxide stream from separation 16 of FIG. 4, usually being of higher purity than the recycle stream obtained from recovery 17, may be preferentially fed to reacting step 14a while the mother liquor recycle stream obtained from recovery 17 may be fed to the reacting step 14b of FIG. 2.

To prevent a progressive build-up of impurities within the system, a part of either or both streams recovered from separation 16 and recovery 17 is bled from the system and discarded or subjected to additional purification operations prior to return to the system. Typically, the amount of the bleed stream ranges from about 1 to about 50 percent of the "solids" involved in the streams, the amount of the bleed usually being no more than that which is necessary to maintain a suitable purity within the system. Of course, it is to be understood that where suitable external utilization of the streams from separation 16 and recovery 17 is available, that it may be preferred to feed fresh reactant at steps 14, 14a, and 14b or 100 percent of the requirements of the system at those points rather than merely feeding makeup requirements. Alternatively, either or both of the streams from separation 16 and recovery 17 may be subjected in toto to additional purification or recovery operations prior to recycle to 14, 14a or 14b rather than merely subjecting a bleed fraction thereof to such intermediate or intervening recovery or purification operations.

The following examples indicate preferred embodiments of the present invention.

EXAMPLE 1

3.0 Grams (16.3 millimols) of 3-carbamoyl-3-hydroxy-4-chlorobutyric acid was added to 30 cc of water. One gram (90 percent pure, 17.8 millimols) of calcium oxide was added at room temperature to form the calcium salt and to epoxidize. The proportions correspond to about 1 gram-atom of alkaline earth metal per gram-mol of 3-carbamoyl-3-hydroxy-4-chlorobutyric acid. Then 0.8 gram (16.3 millimols) of sodium cyanide was added at room temperature. A small amount of precipitate was formed after about 3 hours. The system was filtered providing 1.8 grams of a white insoluble material. The filtrate was then heated to 60°C and maintained at that temperature for one hour. An additional amount of precipitate formed and was recovered by filtration providing an additional 1.7 grams of a white, water-insoluble precipitate. The total weight of precipitate thus recovered was 3.5 grams. The precipitate was analyzed by NMR (nuclear magnetic resonance) and by infrared spectroscopy showing a citrate precursor structure with a form of the carbamoyl radical

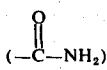

in place of one of the carboxylate

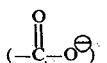

radicals of the actual citrate structure. The product was an adduct which was soluble initially until ammonia was removed from the system on standing.

EXAMPLE 2

Example 1 was repeated to provide a quantity of adduct for elemental analysis providing 5.1 grams of solids which analyzed as follows:

| Element | Wt. Percent |
|---------|-------------|
| N       | 4.03        |
| Ca      | 21.5        |
| Na      | 0.09        |
| Cl      | <0.008      |

The solids were analyzed by vapor phase chromatography and shown to contain 2.1 wt. percent citric acid. On analysis by nuclear magnetic resonance, the solids provided a citrate spectrum corresponding to an acid amide consistent with the citric acid precursor structure expected. The yield of hydroxy monoamide dicarboxylate based on the nitrogen present was 91 percent.

EXAMPLE 3

Ten Grams (55 millimols) of 3-carbamoyl-3-hydroxy-4-halobutyric acid were combined with 100 cc of water and 3.6 grams of 90 percent CaO (56 millimols). The system was agitated for one-half hour at room temperature and then 4.15 grams (85 millimols) of sodium cyanide was added. The system was then agitated for 3 hours at room temperature. The system pH was 11 to 11.3. Then 1.8 grams additional calcium oxide (28 millimols) were added. The system at this point was divided into two portions, A and B.

Portion A was agitated for 1½ hours at 50°-56°C, then for 30 minutes at 70°C, then for 15 minutes at 100°C. The resulting system was filtered, the solids washed with water and 0.7 gram (12 millimols) of calcium oxide was added to the filtrate. The system was heated for 15 minutes and filtered, providing 16.1 grams of solid precipitate. The system analyzed 23.5 wt. percent calcium, 4.35 wt. percent nitrogen and 19.0 percent total carbon.

Six grams of the recovered precipitate were reacted with 4 grams of sodium carbonate and 4 grams of sodium hydroxide at reflux for 6 hours and then was allowed to stand at room temperature for 1 week. The resulting system was analyzed by vapor phase chromatography after reaction with diazomethane to form methyl esters. The yield was 79 percent sodium citrate equivalent.

The second (B) portion produced in the foregoing was allowed to stand at room temperature for about 40 hours and then was heated at 50°-100°C for one hour. The system was filtered, the precipitate washed and 0.7 gram of additional calcium oxide was added to the filtrate. The precipitate was recovered and weighed at 18.87 grams. The precipitate was analyzed by the pentabromoacetone method. In this method, the sample is solubilized in aqueous $H_2SO_4$, then treated with potassium bromide solution. Potassium permanganate solution is then added liberating bromine which oxidizes the citrate to form pentabromoacetone. Following the oxidation, excess bromine is removed by treatment with ferrous ammonium sulfate, the PBA is extracted with chloroform and the amount of PBA in the chloroform layer is analyzed by I.R. spectrophotometry measurement at 3.05 millimicrons. The yield was 97 percent based on starting material. The precipitate recovered was analyzed and found to contain 22.5 wt. percent calcium, 3.95 wt. percent nitrogen and 22.5 percent total carbon.

EXAMPLE 4

Example 3 was repeated; however, an equal molar amount of cyanide (—CN) from calcium cyanide was used in place of the sodium cyanide. Yield of the calcium adduct was determined by the pentabromoacetone method as 86 percent.

A portion of the adduct was hydrolyzed with 4.5 grams of $Na_2CO_3$ and 1.0 gram of NaOH by refluxing at 110°-115°C for 8 hours. After 1 week standing at room temperature, the product was analyzed by V.P.C. and showed approximately 81 percent yield of citric acid based on the 3-carbamoyl-3-hydroxy-4-chlorobutyric acid.

EXAMPLE 5

A solution containing 50.5 millimols of 3-carbamoyl-3-hydroxy-4-chlorobutyric acid in 40 ml of water containing 60 millimols of HCN (9.5 millimols excess) was treated with 82 millimols of calcium oxide added slowly while maintaining a temperature of about 25°C. The excess of calcium oxide above a 1.5 ratio of gram-atoms of calcium per gram-mol of 3-carbamoyl-3-hydroxy-4-chlorobutyric acid was used to neutralize impurities contained in the 3-carbamoyl-3-hydroxy-4-chlorobutyric acid. When the addition was complete, the solution was warmed to 45°C and held at that temperature for about 1 hour.

The resulting solution was treated with concentrated HCl added to produce a pH of 1.5 (approximately 0.18 mol of HCl was added) and maintained at this pH by incrementally adding HCl during a three hour reflux at about 105°C at atmospheric pressure. The resulting solution was analyzed by nuclear magnetic resonance showing virtually quantitative conversion of the starting material to citric acid.

This example involved proportions of approximately 1 gram-mol of cyanide and approximately 1.5 gram-atoms of calcium per gram-mol of 3-carbamoyl-3-hydroxy-4-chlorobutyric acid providing a soluble adduct which was converted to citric acid using acid hydrolysis.

EXAMPLE 6

A solution containing 50.5 millimols of 3-carbamoyl-3-hydroxy-4-chlorobutyric acid in 40 ml of water was treated with 55 millimols of calcium oxide added slowly while maintaining a temperature of about 25°C. The excess calcium oxide above a one gram-atom of calcium per gram-mol of 3-carbamoyl-3-hydroxy-4-chlorobutyric acid was used to neutralize impurities contained in the 3-carbamoyl-3-hydroxy-4- chlorobutyric acid. After 15 minutes, 55 millimols of solid sodium cyanide was added and the system was reacted for 1 hour at 40°C. The amount of sodium cyanide indicated includes about 10 percent excess of $(CN)^-$. The system was analyzed at this point by nuclear magnetic resonance, the results of the analysis indicating that the cleavage of the epoxide ring was complete. Then 42 millimols of calcium oxide was added and the mixture was stirred at 45°C for 5 hours and then at 90°C for 1½ hours. Ammonia was evolved and allowed to escape. A white precipitate formed in the system and was recovered by filtration, then dried, weighed, analyzed and found to represent a 92.8 percent yield of insoluble calcium adduct.

The adduct was then subjected to base hydrolysis wherein 20.4 millimols of the adduct in 40 ml of water was treated with 100 millimols of sodium hydroxide and heated for 8 hours at 60°C and then for one hour at 95°C. The resulting product was analyzed by nuclear magnetic resonance indicating a yield of 96.8 percent sodium citrate. Analysis of the same composition by vapor phase chromatography wherein the sodium citrate was converted to trimethyl citrate indicated a yield of sodium citrate of 92.2 percent.

In this example the ratios were 1.85 gram-atoms of alkaline earth metal and about 1.1 gram-atoms of alkali metal per gram-mol of 3-carbamoyl-3-hydroxy-4-chlorobutyric acid and an insoluble adduct was produced.

EXAMPLE 7

Example 5 was repeated using a solution containing 146 millimols of 3-carbamoyl-3-hydroxy-4-chlorobutyric acid in 75 ml of water, 172 millimols of HCN (26 millimols excess) and 320 millimols of calcium oxide, the latter being added in two portions (240 millimols and 80 millimols) similar to Example 6. The excess calcium oxide above a ratio of 2.0 gram-atoms of calcium per gram-mol of 3-carbamoyl-3-hydroxy-4-chlorobutyric acid was used to neutralize impurities contained in the 3-carbamoyl-3-hydroxy-4-chlorobutyric acid.

The insoluble calcium adduct was recovered and analyzed and corresponded to virtually quantitative yield.

In this example, substantially 2 gram-atoms of alkaline earth metal and no alkali metal were used per gram-mol of 3-carbamoyl-3-hydroxy-4-chlorobutyric acid.

EXAMPLE 8

Example 5 was repeated; however, hydrolysis was with $H_2SO_4$ instead of HCl. In addition, the reactant amounts were based on 52.7 millimols of 3-carbamoyl-3-hydroxy-4-chlorobutyric acid, other reactants (except the $H_2SO_4$) being used in the same proportions as in Example 5.

The $H_2SO_4$ was used in proper proportions (198 millimols) to precipitate calcium as the sulfate and to produce and maintain a pH of 1.5 in a 2 hour hydrolysis at 105°–110°C.

The resulting citric acid solution was filtered to remove precipitated $CaSO_4$ and the filtrate was analyzed by N.M.R. showing virtually quantitative yield of citric acid.

EXAMPLE 9

Example 5 is repeated using 50.5 millimols of NaCN instead of HCN and using 50.5 millimols of calcium oxide. This provides 1 gram-atom of calcium and 1 gram-atom of sodium, producing a soluble adduct. Similar results are obtained.

EXAMPLE 10

100 Millimols of 3-oxo-4-chlorobutyric acid is dissolved in 100 ml of water containing 250 millimols of HCN. 10 Millimols of calcium oxide is added and the mixture is stirred at 25°C for 4 hours. This produces 3-cyano-3-hydroxy-4-chlorobutyric acid.

The 3-cyano-3-hydroxy-4-chlorobutyric acid from the preceding step is hydrolyzed to produce 3-carbamoyl-3-hydroxy-4-chlorobutyric acid by heating the aqueous system for about 2 hours at 50°C. This produces an aqueous solution similar to that used in Examples 5–8.

In accordance with the foregoing proportions, 215 millimols of calcium oxide is reacted with the entire product of the preceding preparation described in this example to produce an insoluble adduct based on the use of about 2 gram-atoms of alkaline earth metal per gram-mol of 3-carbamoyl-3-hydroxy-4-chlorobutyric acid.

EXAMPLE 11

To 50 cc of water was added 8.9 grams (46.5 millimols) of 3-carbamoyl-3-hydroxy-4-chlorobutyric acid. To this was added 8.2 grams of 98 percent barium hydroxide (46.5 millimols). This system was agitated for 30 minutes at room temperature, then 2.3 grams (46.5 millimols of sodium cyanide) was added and the resulting system agitated for 3 hours at room temperature. Then 4.1 grams (23.3 millimols) of barium hydroxide was added and the system agitated for 3 hours at 50°–60°C followed by an agitation for 30 minutes at reflux of the water. The resulting system was filtered yielding 18 grams of solid adduct. The adduct was analyzed and found to contain 31.2 millimols of a mixture of barium citrate and barium adduct.

I claim:

1. A process for producing citric acid or salts thereof which comprises reacting a 3-carbamoyl-3-hydroxy-4-halobutyrate in an aqueous system with about 1 gram mol of cyanide ion and at least about 1 gram mol of alkaline earth metal hydroxide per gram mol of 3-carbamoyl-3-hydroxy-4-halobutyrate under conditions which form an alkaline earth metal adduct, and subjecting said adduct to hydrolysis under alkaline or acidic conditions to form a citrate.

2. The process of claim 1 wherein the alkaline earth metal hydroxide is calcium hydroxide.

3. The process of claim 1 wherein the alkaline earth metal hydroxide is calcium hydroxide and the amount thereof employed is sufficient to cause an adduct to precipitate from solution.

4. The process of claim 1 wherein the alkaline earth metal hydroxide is calcium hydroxide, wherein the amount employed is sufficient to cause an adduct to precipitate from solution, and wherein the precipitated adduct is separated from the resulting solution prior to the hydrolysis.

5. The process of claim 1 wherein the hydrolysis is conducted under alkaline conditions.

6. The process of claim 1 wherein the hydrolysis is conducted under acidic conditions.

7. The process of claim 1 wherein the alkaline earth metal hydroxide is calcium hydroxide, the amount thereof employed is sufficient to cause an adduct to precipitate from solution, wherein the precipitated adduct is separated from the resulting solution prior to the hydrolysis, and wherein the hydrolysis is conducted under alkaline conditions.

8. The process of claim 1 wherein the alkaline earth metal hydroxide is calcium hydroxide, the amount thereof employed is sufficient to cause an adduct to precipitate from solution, wherein the precipitated adduct is separated from the resulting solution prior to the hydrolysis, and wherein the hydrolysis is conducted under acidic conditions.

9. The process of claim 1 wherein the alkaline earth metal hydroxide is calcium hydroxide, the amount thereof employed is sufficient to cause an adduct to precipitate from solution, wherein the precipitated adduct is separated from the resulting solution prior to the hydrolysis, and wherein the hydrolysis utilizes sodium hydroxide.

10. The process of claim 1 wherein the alkaline earth metal hydroxide is calcium hydroxide, the amount thereof employed is sufficient to cause an adduct to precipitate from solution, wherein the precipitated adduct is separated from the resulting solution prior to the hydrolysis, and wherein the hydrolysis utilizes hydrochloric acid.

11. The process of claim 1 wherein the 3-carbamoyl-3-hydroxy-4-halobutyrate is 3-carbamoyl-3-hydroxy-4-chlorobutyric acid.

12. The process of claim 1 wherein the alkaline earth metal hydroxide and 3-carbamoyl-3-hydroxy-4-halobutyrate are used in the molar proportions of from about 1:1 to about 2:1 and wherein the cyanide and the 3-carbamoyl-3-hydroxy-4-halobutyrate are used in the molar proportions of about 1:1.

13. The process of claim 1 wherein excess alkaline earth metal hydroxide and excess cyanide fed to the system are recovered and recycled.

14. The process of claim 1 wherein the 3-carbamoyl-3-hydroxy-4-halobutyrate is 3-carbamoyl-3-hydroxy-4-chlorobutyrate and the alkaline earth metal hydroxide is calcium hydroxide.

15. A process for producing citric acid or salts thereof which comprises:
reacting 3-oxo-4-chlorobutyric acid with HCN in an aqueous system to form 3-cyano-3-hydroxy-4-chlorobutyric acid,
reacting 3-cyano-3-hydroxy-4-chlorobutyric acid with water at a pH of from about 1.0 to about 3.0 to form 3-carbamoyl-3-hydroxy-4-chlorobutyric acid,
reacting 3-carbamoyl-3-hydroxy-4-chlorobutyric acid in an aqueous system with about 1 gram-mol of cyanide and at least about 1 gram-mol of alkaline earth metal hydroxide per gram-mol of 3-carbamoyl-3-hydroxy-4-chlorobutyric acid to form an alkaline earth metal adduct, and
reacting said adduct with alkali metal hydroxide, oxide or carbonate or with mineral acid to produce alkali metal citrate or citric acid.

16. The process of claim 15 wherein at least about two gram-mols of cyanide are provided per gram-mol of 3-oxo-4-chlorobutyric acid and wherein the excess cyanide is retained in the system after the first step for the subsequent reaction of 3-carbamoyl-3-hydroxy-4-chlorobutyric acid with cyanide and with alkaline earth metal hydroxide.

17. The process of claim 15 wherein the alkaline earth metal hydroixde is calcium hydroxide.

18. The process of claim 15 wherein the alkaline earth metal hydroxide is calcium hydroxide and wherein the cyanide is provided by feeding HCN.

19. A process for producing an intermediate compound hydrolyzable to citric acid or its salts which comprises: forming an aqueous solution containing 3-carbamoyl-3-hydroxy-4-halobutyrate ions, cyanide and alkaline earth metal ions in proportions of at least 1 gram-mol of cyanide and one gram-atom of alkaline earth metal per gram-mol of 3-carbamoyl-3-hydroxy-4-halobutyrate, and reacting said system at from about 0 to about 100°C to produce an alkaline earth metal adduct hydrolyzable to citric acid or its salts.

20. The process of claim 19 wherein the reacting step is conducted at from about 0° to about 50°C for from about 1 minute to about 4 hours and in a subsequent stage at a temperature at least about 10° higher than the first stage at from about 50° to about 100°C for from about ½ to about 10 hours.

21. The adduct produced by reacting a 3-carbamoyl-3-hydroxy-4-halobutyrate in an aqueous system with cyanide and alkaline earth metal hydroxide in proportions of about 1 gram-atom of cyanide, and from about 1 to about 2 gram-mols of alkaline earth metal hydroxide per gram-mol of 3-carbamoyl-3-hydroxy-4-halobutyrate.

22. The adduct of claim 21 wherein the alkaline earth metal hydroxide is calcium hydroxide.

* * * * *

UNITED STATES PATENT OFFICE
CERTIFICATE OF CORRECTION

PATENT NO. : 3,962,287
DATED : June 8, 1976
INVENTOR(S) : Karl E. Wiegand

It is certified that error appears in the above-identified patent and that said Letters Patent are hereby corrected as shown below:

Column 6, line 10, reads "halobuyric", should read -- halobutyric --. Columns 5 and 6, Equation 2, remove "→" (second occurrence). Column 7, line 61, reads "$(CN)^-$", should read -- $(CN)^\ominus$ --. Column 9, line 8, reads "$(CN)^-$", should read -- $(CN)^\ominus$ --. Column 10, line 34, reads "$(CN)^-$", should read -- $(CN)^\ominus$ --; line 37, reads "$(CN)^-$", should read -- $(CN)^\ominus$ --; line 46, reads "3oxo-4-", should read -- 3-oxo-4- --. Column 11, line 30, reads "3,4epoxybutyrate", should read -- 3,4-epoxybutyrate --. Column 12, line 32, reads "is present", should read -- if present --; line 45, reads "This", should read -- Thus --. Column 15, line 21, reads "not", should read -- now --. Column 22, line 22, reads "hydroixde" (first occurrence), should read -- hydroxide --.

Signed and Sealed this

Twenty-second Day of March 1977

[SEAL]

Attest:

RUTH C. MASON
Attesting Officer

C. MARSHALL DANN
Commissioner of Patents and Trademarks